United States Patent [19]
Yamada

[11] Patent Number: 5,399,316
[45] Date of Patent: Mar. 21, 1995

[54] REACTION VESSEL FOR CONDUCTING AN IMMUNOLOGICAL ASSAY

[75] Inventor: Takashi Yamada, Sagamihara, Japan

[73] Assignee: Olympus Optical Co., Ltd., Tokyo, Japan

[21] Appl. No.: 25,833

[22] Filed: Mar. 3, 1993

[30] Foreign Application Priority Data

Mar. 13, 1992 [JP] Japan .................................. 4-055115

[51] Int. Cl.⁶ ................. G01N 33/543; G01N 33/546; G01N 33/552
[52] U.S. Cl. ........................................ 422/58; 422/57; 422/101; 422/102; 422/104; 435/5; 435/7.92; 435/805; 435/970; 436/165; 436/172; 436/518; 436/524; 436/527; 436/528; 436/533; 436/805; 436/807; 436/808; 436/810
[58] Field of Search ............... 436/518, 524, 527, 528, 436/533, 172, 807–810, 805, 165; 435/5, 7.92, 805, 962, 968, 970; 422/57, 58, 101, 102, 104

[56] References Cited

U.S. PATENT DOCUMENTS

| | | | |
|---|---|---|---|
| 3,981,100 | 9/1976 | Weaver et al. | 47/56 |
| 4,134,863 | 1/1979 | Fanta et al. | 128/285 |
| 4,155,888 | 5/1979 | Mooth | 260/17.4 GC |
| 4,426,451 | 1/1984 | Columbus | 436/518 |
| 4,596,695 | 6/1986 | Cottingham | 422/58 |
| 4,849,340 | 7/1989 | Oberhardt | 435/7 |
| 4,902,629 | 2/1990 | Meserol et al. | 422/58 X |
| 5,066,465 | 11/1991 | Kano et al. | 422/58 |
| 5,147,607 | 9/1992 | Mochida | 422/58 X |
| 5,188,968 | 2/1993 | Kano et al. | 422/58 X |
| 5,196,302 | 3/1993 | Kidwell et al. | 422/57 X |
| 5,209,904 | 5/1993 | Forney et al. | 422/58X |

OTHER PUBLICATIONS

The "OPUS" System in Immunoassay Automation A Practical Guide; edited by Daniel W. Chan; Academic Press Inc., California; pp. 245–267.

Primary Examiner—Carol E. Bidwell
Assistant Examiner—Christopher L. Chin
Attorney, Agent, or Firm—Frishauf, Holtz, Goodman & Woodward

[57] ABSTRACT

A sample solution is dripped on an injection region with a pipette. The sample solution immediately spreads in a reaction region by a capillary phenomenon. The sample solution is left for a predetermined period of time to bind a biological associated material in the sample solution with a specific affinity material bound on the inner surface of the reaction region. After the reaction, the outer surface portion of a support member is pushed against a reaction vessel main body to deform the support member, thereby bringing the sample solution into contact with a water absorbent member at a removal region. The sample solution is absorbed by the water absorbent member and is removed from the reaction region. A cleaning solution is dripped on the injection region in an appropriate amount to perform B/F separation and is allowed to spread in the reaction region. The cleaning solution is absorbed and removed by the water absorbent member. The biological associated material bound to the reaction region is assayed.

11 Claims, 1 Drawing Sheet

REACTION VESSEL FOR CONDUCTING AN IMMUNOLOGICAL ASSAY

BACKGROUND OF THE INVENTION

1. Field of the Invention

The present invention relates to a method of assay of a biological associated material. The present invention also relates to a reaction vessel used in the assay of the biological associated material.

2. Description of the Related Art

Biological associated materials (i.e., material contained in a body fluid) have been assayed as daily examinations in the medical and environmental sanitation fields. Particularly, in the medical field, various types of biological associated materials have been assayed in many medical centers to diagnose diseases and to evaluate therapeutic effects for diseases. Examples of the biological associated material are biological constituent materials such as various proteins (including antibodies), polypeptides, saccharides, nucleic acid, lipids, and various hormones represented by steroid, in addition to extravital materials such as various pathogenic microorganisms, an allergen for causing an allergic reaction, and drugs for causing biological reactions. The particular materials having a relevance to generation of contagious diseases or cancer and cause an antigen-antibody reaction or a reaction between a nucleic acid and another complementary nucleic acid.

Such a biological associated material is assayed in a reaction with a specific affinity material having a specific affinity with this biological associated material. For example, using an antigen-antibody reaction as one of the reactions between a biological associated material and a corresponding specific affinity material, infectious diseases such as acquired immunodeficiency syndrome (to be referred to as AIDS hereinafter) as the most critical current topic in public health can be examined, and cancer associated materials which can hardly be conventionally specified can be assayed.

A DNA or RNA as a gene of an infectious microorganism can also be assayed using a complementary nucleotide which binds to the characteristic portion of the polynucleotide of the DNA or RNA. The reaction between the polynucleotide and complementary nucleotide is one of the reactions between the biological associated materials and the corresponding specific affinity materials. A reaction between insulin as one of hormones and an insulin receptor is one of the reactions between the biological associated materials and the corresponding specific affinity materials.

In this manner, various methods of assaying biological associated materials using reactions with specific affinity materials are known. In any method, the amount of a biological associated material (to be referred to as a bound material hereinafter) to which a specific affinity material is bound must be assayed.

These methods of assaying the biological associated materials are mainly classified into two methods. The first method is an assay for detecting a bound material by utilizing a change in nature of a specific affinity material itself or a tracer combined thereto upon binding of the specific affinity material to the bound material. This first method has been called a homogenous assay. The second method is an assay for performing B (Bound)/F (Free) separation for separating a bound material from a free material after a complex of a specific affinity material and a bound material is set insoluble by any means. The second method has been called a heterogeneous assay.

As the heterogeneous assay, a method is also known in which a second specific affinity material which specifically binds to a complex of a specific affinity material and a bound material is bound to the complex so that the size of the complex molecule is increased, thereby setting the complex insoluble. This method, however, is not preferable due to poor reliability in assay precision. In order to solve this problem, the following B/F separation is generally performed. A specific affinity material is bound to an insoluble material. Thereafter, the specific affinity material is reacted with a biological associated material so as to form a complex of the biological associated material, the specific affinity material and the insoluble material, and then the complex is separated from a sample solution. Examples of the insoluble material are a reaction tube, beads, or filter paper.

In the heterogeneous assay, when a reaction tube itself is used as an insoluble material, the reaction tube is used only once and need not be cleaned, thus requiring a relatively small amount of cleaning water. However, waste products tend to increase in amount, resulting in inconvenience. This assay is not suitable for treating a large number of samples. In addition, the substantial reaction between the biological associated material and the specific affinity material is assumed to occur on the surface of the reaction tube. For this reason, a sample and a reagent which cannot be reacted with the specific affinity material are presented, and are wasted, resulting in inconvenience.

To the contrary, when a material such as beads or filter paper except for the reaction tube is used as an insoluble material, the reaction tube can be repeatedly used. However, since the reaction tube must be cleaned, an assay operation becomes cumbersome. If the operation is automated, the resultant apparatus becomes bulky. The sample to be examined tends to be left (so-called carry-over) in the insoluble material.

In addition, the precision and efficiency of heterogeneous assay depend on whether B/F separation is effectively performed. When the reaction tube is used as an insoluble material, the reaction tube can be relatively easily separated from a sample solution. To the contrary, when an insoluble material except for the reaction tube is used, for example, a filter is used to separate the insoluble material from the sample solution, or an insoluble material is agglutinated and separated by a centrifugal or magnetic force. For this reason, it is difficult to precisely perform B/F separation at high speed.

As a means for solving the disadvantage of the conventional heterogeneous assay described above, the present applicant proposes a novel method for assay of a biological associated material (U.S. Pat. No. 5,066,465). A reaction vessel used in this method has a sample inlet channel having a sectional area capable of drawing a sample in the reaction vessel by a capillary phenomenon, a recess formed in the inner wall of the sample inlet channel, and a transparent plate disposed above the recess and having a flat surface for defining the upper limit of a reaction region. In this method, a sample is dripped in the sample inlet channel to cause a predetermined amount of the sample to be absorbed in the reaction region by the capillary phenomenon, and a pattern of agglutinated particles is formed in the recess, thereby analyzing the biological associated material.

This method is suitable for an assay using a very small amount of a sample.

Since a reaction between a biological associated material and a specific affinity material generally requires a reaction time of minutes to tens of minutes, a sample solution must be caused to stay in the reaction vessel for a predetermined period of time. On the other hand, in cleaning the reaction vessel, the cleaning solution unlike the sample solution need not stay in the reaction vessel and must be quickly removed. As a method of assay of a biological associated material using the above reaction vessel, it has been desired earnestly to develop a new method of efficiently holding a solution in a reaction vessel and removing the solution from the reaction vessel so as to perform a more efficient operation.

In order to satisfy the above demand, an evacuation unit is arranged at one end of the sample inlet channel to draw the cleaning solution in the reaction vessel having the above arrangement. However, to perfectly clean the reaction vessel, the cleaning solution must be continuously supplied to the reaction vessel for a predetermined period of time. For this purpose, a cleaning solution supply unit capable of continuously supplying the cleaning solution must be arranged at the other end of the sample inlet channel. Although the reaction vessel itself can be made compact, the resultant apparatus becomes bulky. As a result, a method of assay of a biological associated material using a compact apparatus in a small test center cannot be provided.

SUMMARY OF THE INVENTION

It is an object of the present invention to provide a method of assay of a biological associated material and a reaction vessel used in the method, wherein a sample solution and a cleaning solution can be easily removed from the reaction vessel by a simple means.

That is, according to an aspect of the present invention, there is provided a method of assay of a biological associated material, including the steps of holding the biological associated material in a sample solution with a specific affinity material in a reaction vessel for a predetermined period of time so as to react them, the specific affinity material having a specific affinity with the biological associated material bound to an insoluble material, removing the sample solution from the reaction vessel, cleaning the reaction vessel with a cleaning solution to separate the biological associated material bound to the specific affinity material from a free material, and assaying the separated biological associated material, wherein a water absorbent member having a sufficiently high water absorbency is brought into contact with the sample solution or the cleaning solution at an appropriate timing so as to cause the water absorbent member to absorb the sample solution or the cleaning solution, thereby controlling a holding time of the sample solution or the cleaning solution in the reaction vessel.

According to another aspect of the present invention, there is provided a reaction vessel comprising a reaction vessel main body in which a reaction region capable of holding a sample solution or a cleaning solution is formed to extend through an interior thereof and at least one of side surface portions is constituted by a transparent member, a water absorbent member disposed at a position spaced apart from an opening at one end of the reaction region by a predetermined distance, and a support member for supporting the water absorbent member to be brought into contact with or separated from the sample solution or the cleaning solution.

According to the method of assay of the biological associated material of the present invention, after the sample solution or the cleaning solution is held in the reaction vessel for the predetermined period of time, the water absorbent member is brought into contact with this solution and absorbs it. Therefore, the sample solution or the cleaning solution can be efficiently removed by a relatively simple means from the reaction vessel.

According to the reaction vessel of the present invention, when the sample solution or the cleaning solution is held in the reaction region, the water absorbent member is separated from the solution by the support member. When the sample solution or the cleaning solution is to be removed, the water absorbent member is brought into contact with the solution, thereby causing the water absorbent member to absorb the sample solution or the cleaning solution.

According to the present invention, the sample solution or the cleaning solution held in the reaction vessel can be removed by the relatively simple means. In addition, the amount of the cleaning solution required for B/F separation can be greatly reduced. According to the reaction vessel of the present invention, since the water absorbent member is brought into contact with the sample solution or the cleaning solution by the support member, this solution can be efficiently removed from the reaction region by a simple arrangement. As a result, the time-consuming operation required for assaying a biological associated material can be facilitated, and the apparatus of assay as a whole can be easily made compact.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWING

The accompanying drawing, which is incorporated in and constitutes a part of the specification, illustrates a presently preferred embodiment of the invention and, together with the general description given above and the detailed description of the preferred embodiment given below, serves to explain the principles of the invention.

DETAILED DESCRIPTION OF THE PREFERRED EMBODIMENT

Figure 1:
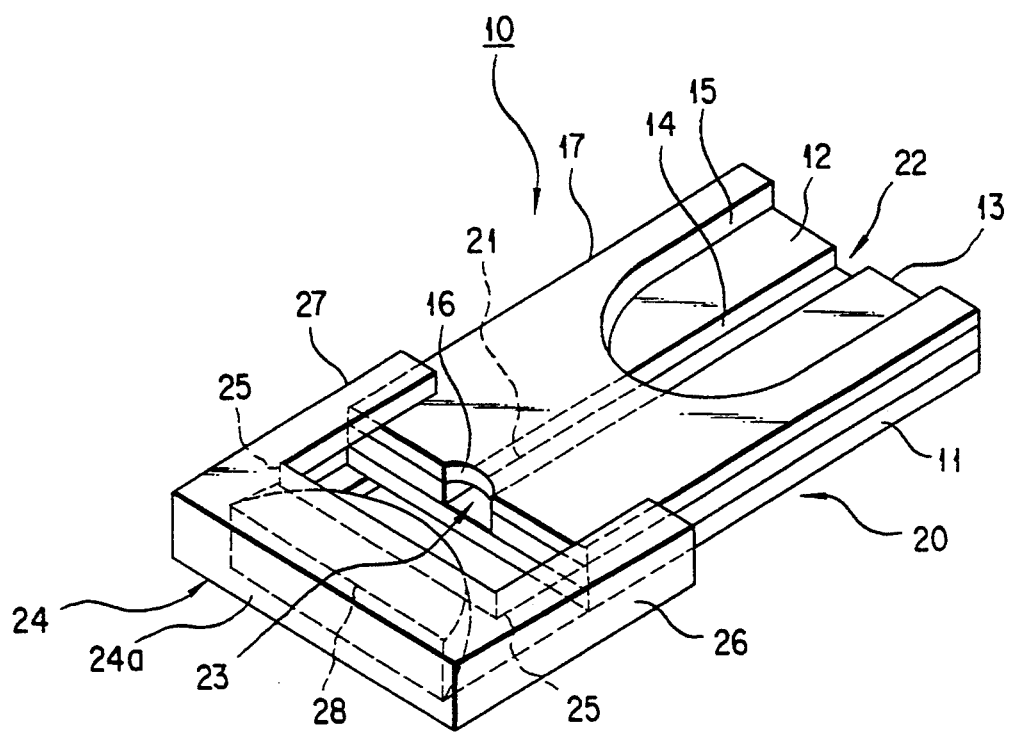
FIG. 1 is a perspective view for explaining a structure of a reaction vessel used in a method of assay of a biological associated material according to the present invention.

A preferred embodiment of the present invention will be described with reference to the accompanying drawing.

The reaction vessel 10 comprises a base member 11 of an almost flat and rectangular shape. Two spacers 12 and 13 are disposed to be spaced apart from each other by a predetermined distance on the major surface of the base member 11, thereby forming a groove 14. A cover 17 is placed on the major surfaces of the spacers 12 and 13. In the cover 17, an almost U-shaped notched portion 15 having a width larger than that of the groove 14 is formed in the portion which corresponds to one end portion of the groove 14, and a recess 16 having a width almost equal to that of the groove 14 is formed in a portion which corresponds to the other end portion of the groove 14. The base member 11, the spacers 12 and 13, and the cover 17 are adhered to each other.

In a reaction vessel main body 20 having the above arrangement, a reaction region 21 surrounded by the base member 11, the spacers 12 and 13, and the cover 17, an injection region 22 defined by the notched portion 15, the base member 11, and the spacers 12 and 13, and a removal region 23 defined by the recess 16 and the groove 14 are formed.

The thickness of each spacer 12 or 13 and the width of the groove 14 in the reaction vessel main body 20 are preferably set such that a sample solution or the like spreads in the reaction region 21 by a capillary phenomenon when the sample solution or a cleaning solution is injected in the injection region 22. More specifically, the thickness of each spacer 12 or 13 preferably falls within the range of 0.1 to 1.0 mm, and more particularly about 0.5 mm. The width of the groove 14 is preferably slightly larger than the distal end portion of a pipette normally used and falls within the range of, e.g., 3 to 5 mm.

The reaction region 21 is elongated and extends at almost the center of the main body 20, and the sample solution or the like can be dispersed in the entire area of the reaction region 21 at an almost uniform rate. When the width of the reaction region 21 is excessively large, the dispersion rate becomes nonuniform, and the cleaning efficiency may be degraded.

When the groove 14 of the reaction region 21 covered with the cover 17 is elongated, the surface area of the reaction region 21 is increased accordingly. The level of a signal obtained as a result of the reaction is preferably increased. Since a portion exposed from the cover 17 is large, this portion can store an excessive portion of the amount of reagent or the like which exceeds the capacity of the reaction region 21. For this reason, a strict limitation is not imposed on the amount of reagent or the like if the amount exceeds the capacity of the reaction region 21.

when the assay of a biological associated material is to be performed by measuring fluorescence or luminescence induced due to the presence of the biological associated material itself or a material bound to the biological associated material, one of the base member 11 and the cover 17 must be made of a transparent material. Examples of the transparent materials are various polymer materials such as cellulose acetate, polyethyleneterephthalate, polycarbonate and polystyrene. In addition, an inorganic material such as glass can also be used.

To combine a specific affinity material to the base member 11, the spacers 12 and 13, or the cover 17, the material thereof must be selected in accordance with the specific affinity material. Examples of the base member 11, the spacers 12 and 13, or the cover 17 are various polymer materials such as cellulose acetate, polyethyleneterephthalate, polycarbonate and polystyrene. In addition, an inorganic material such as glass can also be used.

Physical adsorption or a chemical covalent bond can be applied to a technique for binding a specific affinity material.

A support member 24 made of an elastic member is connected to the end portion of the reaction vessel main body 20 at which the removal region 23 is formed.

More specifically, the support member 24 has arm portions 26 and 27 having fitting grooves 25 which are formed at the inner side edge portions to fit on the reaction vessel main body 20. A water absorbent member 28 is disposed to oppose the end face of the reaction vessel main body 20. It is desirable that the water absorbent member 28 should have an almost semispherical shape because it can properly contact the recess 16 of the cover 17 to properly absorb the reaction or cleaning solution. The reaction vessel main body 20 is fitted and adhered in the fitting grooves 25 at the distal end portions of the arms 26 and 27. In this case, the water absorbent member 28 is disposed apart from the removal region 23 by a predetermined distance. The material of the support member 24 is selected to be deformable when an outer surface portion 24a of the support member 24 which corresponds to the water absorbent member 28 is pushed against the reaction vessel main body 20. Examples of the material of the support member 24 are a member having elasticity as in the transparent material described above and members of hard rubber or various resins in addition to the transparent material. On the other hand, not only the support member 24 is deformed, but also elastic members such as springs are disposed between the inner sides of the arm portions 26 and 27 and the reaction vessel main body 20 to separate the reaction vessel main body 20 from the water absorbent member 28. However, the outer surface portion 24a may be pushed against the reaction vessel main body 20, thereby bringing the support member 24 as a whole to be close to the reaction vessel main body 20.

Examples of the material of the water absorbent member 28 are absorbent cotton, pulp, cloth, sponge, paper, cellulose, carboxymethyl cellulose, and a super absorbent polymer (e.g., grafted starches or polyacrylate polymer) used for sanitary napkins or as a soil water-retention agent in the fields of agriculture and horticulture. Of these materials, the absorbent polymer is most preferable because the water absorbent capacity is high and the absorbed solution tends not to be discharged even if an external pressure acts on it.

The reaction region 21 may be horizontal or vertical if it can hold the reaction solution and the cleaning solution. The retention force of this solution depends on the thickness of the reaction region 21. For example, when a sample solution having a high protein concentration or a reagent containing a surfactant is used, the thickness of the reaction region 21 must be 0.5mm or less. Otherwise, it is difficult to hold the solution in the reaction vessel 10 when the reaction vessel 10 becomes vertical.

A method of assay of a biological associated material using the above reaction vessel 10 will be described below.

A specific affinity material is placed in the reaction region 21. For example, a specific affinity material is chemically or physically bound to at least one surface of the base member 11, the spacers 12 and 13, or the cover 17 in accordance with a conventional method. Alternatively, an insoluble material to which a specific affinity material is bound may be placed in the reaction region 21 so as not to interfere with the flow of the solution inside the reaction region 21.

A sample solution, which is a solution containing a sample such as a body fluid, e.g., blood, urine, or cerebrospinal fluid and a sample solution which is properly pretreated, is dripped in the injection region 22 with a pipette. The sample solution is dripped in an amount to fill the reaction region 21. The dripped sample solution immediately spreads in the reaction region 21 by a capillary phenomenon. The sample solution is left held inside the reaction region 21 for a predetermined period of time, thereby binding the biological associated material in the sample solution with the specific affinity material. In this case, the reaction vessel 10 may be heated to about 37° C. or cooled to a temperature of 10° C. or less, as needed. If the sample solution is left in the reaction region 21 in an open state for a long period of time, it may evaporate and an accurate assay cannot be performed. As a countermeasure against this problem, the reaction vessel 10 may be stored in a high-humidity condition, as needed.

After the reaction, the outer surface portion 24a of the support member 24 is pushed against the reaction vessel main body 20 to deform the support member 24. The water absorbent member 28 is brought into contact with the sample solution held in the reaction region 21 in the removal portion 23. The sample solution is absorbed by the water absorbent member 28 and is removed from the reaction region 21. In this manner, the water absorbent member 28 is kept pushed until the sample solution is perfectly removed from the reaction region 21.

After the sample solution is removed, a cleaning solution is dripped on the injection region 22 in an appropriate amount so as to perform B/F separation and is caused to spread in the reaction region 21. Thereafter, in the same manner as the sample solution described above, the water absorbent member 28 is brought into contact with the cleaning solution in the removal region 23. The cleaning solution is absorbed by the water absorbent member 28 and is removed from the reaction region 21. This operation is repeated several times to separate the biological associated material bound to the specific affinity material from the free material, thereby removing the free material in the reaction region 21. By this operation, the biological associated material can be bound to the reaction region 21 or the insoluble material arranged in the reaction region 21.

To assay the bound biological associated material, a binding material (e.g., an antigen or antibody), which binds to the biological associated material and which holds a material (e.g., luminol, lucigenine, peroxidase, or glucose oxidas) that induces a luminous reaction is dripped on the injection region 22 and allowed to spread in the reaction region 21. After the reaction for a predetermined period of time, the binding material is absorbed by the water absorbent member 28 and is removed from the reaction region 21. By the above operations, the biological associated material, the binding material, and the material for inducing the luminous reaction are bound to the reaction region 21 or the insoluble material.

A biological associated material will be assayed. A material (e.g., hydrogen peroxide water or catalyst metals) for causing a luminous reaction corresponding to the material for inducing the luminous reaction is dripped in the injection region 22 in an appropriate amount and is caused to spread in the reaction region 21. In order to accelerate the luminous reaction, firefly luciferine, a benzothiazole derivative, or the like may be added. After the reaction for a predetermined period of time, the material causing the luminous reaction is absorbed by the water absorbent member 28 and is removed from the reaction region 21. Thereafter, a detection unit of a measuring apparatus such as a photoelectron multiplier is located above the cover 17 which covers the reaction region 21, and the amount of light emitted from the reaction region 21 is measured. In this case, to measure a very small amount of light caused by the luminous reaction, the measurement can be preferably performed in a perfect light-shielded state. The amount of the biological associated material in the sample solution is determined in accordance with a working curve which were previously prepared.

In place of the luminous reaction, fluorescence emitted from a fluorescent material bound to a biological associated material may be measured using the fluorescent material to assay the biological associated material.

As described above, according to the method of assay of a biological associated material of this embodiment, the sample solution and the cleaning solution can be easily removed from the reaction region 21 in the reaction vessel 10 having a relatively simple arrangement. In addition, B/F separation can be efficiently performed using a small amount of a cleaning solution without using an evacuation unit and a cleaning solution continuous supply unit.

This embodiment exemplifies a reaction vessel having a support member using an elastic member. However, the arrangement of the reaction vessel is not limited to this. In the reaction vessel of this embodiment, the reaction region is defined between two flat plates. The structure of the reaction region is not limited to this. However, when the present invention is applied to a reaction vessel having a reaction region capable of drawing or holding a sample solution or the like in a predetermined amount by a capillary phenomenon, the most excellent effect can be obtained. Any reaction vessel having a reaction region having any shape which satisfies the above functions is preferable.

The assay of a biological associated material is not limited to the assay of luminous and fluorescence, but can employ a general method of assaying a biological associated material. In addition, the above method of assay of the biological associated material and the above reaction vessel may be automated using an automatic analysis apparatus, thereby further increasing the operation efficiency.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A reaction vessel for an immunological assay, comprising:
    a reaction vessel body comprising:
        a bottom member;
        a pair of spacer members on said bottom member, said spacer members being spaced apart and defining a linear capillary groove therebetween;
        said linear groove extending through said reaction vessel body and having a predetermined height and substantially uniform width along the length thereof;
        a cover member mounted on said spacer members over and spaced apart from said bottom member, with said spacer members between said bottom member and said cover member;

said bottom member and spacer members defining a liquid receiving section for receiving at least one of a sample solution containing a sample and a cleaning solution for injection into said reaction vessel body;

said bottom member, said spacer members and said cover member defining a reaction section for receiving a sample solution from said liquid receiving section and for carrying out an antigen-antibody binding reaction on a sample solution therein, said reaction section comprising an immobilized antigen or antibody capable of binding a target antibody or antigen respectively;

said reaction section being positioned downstream from said liquid receiving section;

a liquid outlet section positioned downstream from said reaction section for receiving said sample solution from said reaction section after completion of said antigen-antibody binding reaction;

said liquid receiving section, said reaction section and said liquid outlet section all being positioned in a straight line along said linear groove;

at least one of said bottom member and said cover member being transparent;

said liquid outlet section and said liquid receiving section being positioned at opposite ends of said reaction vessel body, wherein said liquid outlet section comprises an outlet which is positioned in a central portion of an end wall of said reaction vessel body; and a support member coupled to said reaction vessel body directly opposite said liquid outlet section, said support member holding a liquid-absorbing member which absorbs said sample solution or said cleaning solution exiting through said liquid outlet section of said reaction vessel body;

said support member comprising:
an outer wall section having an inner surface, said liquid-absorbing member being mounted on said inner surface of said outer wall section; and
two parallel arm portions extending from opposite end portions of said outer wall section, said arm sections being movably connected to side portions of said reaction vessel body;

said linear groove of said reaction vessel body having an inner volume sized to house said sample solution or said cleaning solution which is to be received thereinto via said liquid receiving section and also being sized to define a capillary reaction section capable of containing a predetermined liquid volume therein to permit said sample solution or said cleaning solution to diffuse from said liquid receiving section through said reaction section to said liquid outlet section by capillary action; and said support member being made of an elastic material such that at least said outer wall section thereof is elastically bendable toward said liquid outlet section responsive to a force applied thereto in a direction toward said liquid outlet section, wherein said liquid-absorbing member is held by said support member at a position spaced apart from said liquid outlet section of said reaction vessel body by a predetermined distance, and wherein said liquid-absorbing member is capable of being brought into physical contact with said liquid outlet section of said reaction vessel body to remove said sample solution or said cleaning solution therefrom when said force in a direction toward said reaction vessel body is applied to at least said outer wall section of said elastic support member, thereby controlling an amount of time said sample solution or said cleaning solution is in said reaction vessel body.

2. The reaction vessel of claim 1, wherein said liquid outlet section of said reaction vessel body has a concave portion which is contactable with said water-absorbing member.

3. The reaction vessel of claim 1, wherein said water-absorbing member is semi-circular in shape, and is shaped such that a center of an arcuate portion of the semi-circular shape is positioned to face said outlet section of said reaction vessel body.

4. The reaction vessel of claim 1, wherein said water-absorbing member held by said support member is made of pulp, cloth, sponge, paper, cellulose, carboxymethyl cellulose or water-absorbing polymer.

5. The reaction vessel of claim 1, wherein:
said arm portions are connected to said reaction vessel body with a further elastic member interposed therebetween; and
when a force toward said liquid outlet section is applied to said outer wall section, said further elastic member is constricted to permit said support member to be moved toward said outlet section.

6. The reaction vessel of claim 1, wherein said support member is made of at least one material selected from the group consisting of cellulose acetate, polyethyleneterephthalate, polycarbonate, polystyrene and hard rubber.

7. The reaction vessel of claim 1, wherein:
said bottom member of said reaction vessel body comprises a substantially plate-like bottom member having a main surface;
said pair of spacer members comprise respective spacers arranged a predetermined distance apart from each other on said main surface of said plate-like bottom member;
said cover member covers at least a portion of said spacers and said main surface of said plate-like bottom member; and
said reaction section comprises a free space enclosed by said plate-like bottom member, said cover member and said spacers.

8. The reaction vessel of claim 7, wherein each of said spacers has a thickness of 0.1 to 1 mm in a direction perpendicular to the main surface of said plate-like bottom member, and said spacers are arranged 3 to 5 mm apart from each other so as to define said linear groove therebetween.

9. The reaction vessel of claim 8, wherein each of said spacers has a thickness of 0.1 to 0.5 mm in a direction perpendicular to the main surface of said plate-like bottom member.

10. The reaction vessel of claim 1, wherein said liquid receiving section is arranged to receive a solution containing a body fluid as said sample.

11. The reaction vessel of claim 10, wherein said liquid receiving section is arranged to receive a body fluid selected from the group consisting of blood, urine and cerebrospinal fluid.

* * * * *

UNITED STATES PATENT AND TRADEMARK OFFICE
CERTIFICATE OF CORRECTION

PATENT NO. : 5,399,316
DATED : March 21, 1995
INVENTOR(S) : YAMADA

It is certified that error appears in the above-indentified patent and that said Letters Patent is hereby corrected as shown below:

On the title page, col. 1, line 2, and under Section [54] Title, after "ASSAY", insert --, HAVING A CAPILLARY GROOVE FOR MOVING A SAMPLE TO A REACTION ZONE AND A DEFORMABLE SUPPORT MEMBER FOR BRINGING A LIQUID ABSORBING MEMBER INTO PHYSICAL CONTACT WITH THE REACTION VESSEL TO REMOVE LIQUIDS THEREFROM--

Signed and Sealed this

Twelfth Day of March, 1996

*Attest:*

BRUCE LEHMAN

*Attesting Officer*  *Commissioner of Patents and Trademarks*